(12) United States Patent
Sherry

(10) Patent No.: US 11,497,410 B2
(45) Date of Patent: Nov. 15, 2022

(54) TERAHERTZ REFLECTION IMAGING SYSTEM

(71) Applicant: TIHIVE, Meylan (FR)

(72) Inventor: Hani Sherry, Grenoble (FR)

(73) Assignee: TIHIVE, Meylan (FR)

( * ) Notice: Subject to any disclaimer, the term of this patent is extended or adjusted under 35 U.S.C. 154(b) by 0 days.

(21) Appl. No.: 16/968,458

(22) PCT Filed: May 2, 2019

(86) PCT No.: PCT/FR2019/050254
§ 371 (c)(1),
(2) Date: Aug. 7, 2020

(87) PCT Pub. No.: WO2019/155156
PCT Pub. Date: Aug. 15, 2019

(65) Prior Publication Data
US 2020/0397336 A1    Dec. 24, 2020

(30) Foreign Application Priority Data

Feb. 7, 2018   (FR) ...................................... 1851025

(51) Int. Cl.
*A61B 5/0507* (2021.01)
*G02B 21/36* (2006.01)
(Continued)

(52) U.S. Cl.
CPC .......... *A61B 5/0507* (2013.01); *G02B 21/367* (2013.01); *G06T 5/10* (2013.01);
(Continued)

(58) Field of Classification Search
CPC ............. A61B 5/0507; G01N 21/3563; G01N 21/3581; G01N 21/3586; G02B 21/367;
(Continued)

(56) References Cited

U.S. PATENT DOCUMENTS

| 3,975,729 A * | 8/1976 | Ringer ................... G01S 13/22 342/82 |
| 4,326,252 A * | 4/1982 | Kohno .................. G06T 11/006 378/14 |

(Continued)

FOREIGN PATENT DOCUMENTS

| WO | 2016185010 A1 | 11/2016 |
| WO | 2016196309 A2 | 12/2016 |

OTHER PUBLICATIONS

International Search Report in connection with International Application No. PCT/FR2019/050254 dated May 27, 2019, 9 pages.
(Continued)

*Primary Examiner* — Peter D Le

(57) ABSTRACT

The invention relates to a sensor for a terahertz imaging system which can be integrally produced using a semiconductor technology, comprising a flat substrate (60) made from semiconductor material that is transparent to terahertz radiation, configured to be oriented parallel to an object (12) to be analyzed; and a plurality of terahertz radiation receivers arranged according to a matrix (10) in the substrate. The sensor is lensless and comprises at least one terahertz radiation transmitter arranged in the substrate, so that the radiation emitted by the transmitter is reflected on the object (12) to be analyzed, towards the receivers.

10 Claims, 2 Drawing Sheets

(51) Int. Cl.
   *G06T 5/10* (2006.01)
   *H04N 5/225* (2006.01)
(52) U.S. Cl.
   CPC . *H04N 5/2256* (2013.01); *G06T 2207/10048* (2013.01); *G06T 2207/10056* (2013.01); *G06T 2207/30088* (2013.01)
(58) Field of Classification Search
   CPC . G06T 2207/10048; G06T 2207/10056; G06T 2207/30088; G06T 5/10; H04N 5/2256
   See application file for complete search history.

(56) References Cited

U.S. PATENT DOCUMENTS

| | | | | |
|---|---|---|---|---|
| 5,082,364 | A * | 1/1992 | Russell | G01S 17/36 356/5.15 |
| 5,276,455 | A * | 1/1994 | Fitzsimmons | H01Q 21/0087 342/368 |
| 5,623,145 | A * | 4/1997 | Nuss | G01N 21/3586 250/330 |
| 6,424,298 | B1 * | 7/2002 | Nishikawa | H01Q 21/064 343/700 MS |
| 9,319,578 | B2 * | 4/2016 | Jiang | G06T 5/003 |
| 2001/0029436 | A1 * | 10/2001 | Fukasawa | G01R 31/311 702/117 |
| 2001/0030759 | A1 * | 10/2001 | Hayashi | H04N 1/32309 358/1.9 |
| 2002/0005951 | A1 * | 1/2002 | Fukasawa | G01N 21/3563 356/432 |
| 2003/0178584 | A1 * | 9/2003 | Arnone | G01N 21/3581 250/495.1 |
| 2004/0030255 | A1 * | 2/2004 | Alfano | G01N 21/4795 600/476 |
| 2007/0167752 | A1 * | 7/2007 | Proulx | A61B 8/483 600/437 |
| 2009/0306510 | A1 * | 12/2009 | Hashiba | G01S 15/8927 600/447 |
| 2013/0193324 | A1 * | 8/2013 | Sengupta | G01J 5/0837 250/338.4 |
| 2013/0201343 | A1 * | 8/2013 | Jiang | H04N 5/2254 348/164 |
| 2013/0256518 | A1 * | 10/2013 | George | G02B 26/02 250/237 R |
| 2014/0326890 | A1 * | 11/2014 | Debray | G01J 5/10 250/349 |
| 2014/0367575 | A1 * | 12/2014 | Sengupta | H01L 27/14649 250/349 |
| 2014/0371571 | A1 * | 12/2014 | Tsujita | A61B 5/0095 600/407 |
| 2015/0036038 | A1 * | 2/2015 | Horstmeyer | G01N 23/205 348/342 |
| 2015/0054979 | A1 * | 2/2015 | Ou | G02B 21/367 348/222.1 |
| 2016/0223452 | A1 * | 8/2016 | Milosevic | G03B 15/03 |
| 2016/0344108 | A1 * | 11/2016 | Assefzadeh | H01Q 3/2682 |
| 2017/0111658 | A1 * | 4/2017 | Jiang | H04N 19/60 |
| 2017/0292919 | A1 * | 10/2017 | Mccollough | G01R 27/06 |
| 2019/0179164 | A1 * | 6/2019 | Jiang | G01T 1/295 |
| 2019/0324136 | A1 * | 10/2019 | Amadjikpe | H04B 7/0434 |
| 2021/0084219 | A1 * | 3/2021 | Ito | H04N 5/23229 |

OTHER PUBLICATIONS

Iwami, et al., "Design and Fabrication of a Scanning Near-Field Microscopy Probe with Integrated Zinc Oxide Photoconductive Antennas for Local Terahertz Spectroscopy," Sensors and Materials, vol. 22, No. 3, 2010, 8 pages.
Jiang, et al., "A 320GHz Subharmonic-Mixing Coherent Imager in 0.13μm SiGe BiCMOS," 2016 IEEE International Solid-State Circuits Conference, Session 25, mm-WAVE THz Sensing, 25.5, IEEE, Feb. 3, 2016, 3 pages.
Pfeiffer, et al., "A 0.53 THz Reconfigurable Source Module With Up to 1 mW Radiated Power for Diffuse Illumination in Terahertz Imaging Applications," IEEE Journal of Solid-State Circuits, vol. 49, No. 12, Dec. 2014, 13 pages.
Pfeiffer, et al., "Silicon-based Sources and Detectors for Terahertz Applications," Optical Society of America, STu1F.3, CLEO, 2014, 2 pages.
Sengupta, et al., "Silicon Integrated 280 GHz Imaging Chipset With 4x4 SiGe Receiver Array and CMOS Source," IEEE Transactions on Terahertz Science and Technology, vol. 5, No. 3, May 2015, 11 pages.
Sodini, et al., "Millimeter-Wave Imaging using Silicon Technology," IEEE, 2011, 21 pages.
International Preliminary Report on Patentability with English translation of the Written Opinion in connection with International Application No. PCT/FR2019/050254 dated Aug. 20, 2020, 10 pages.

* cited by examiner

TERAHERTZ REFLECTION IMAGING SYSTEM

CROSS-REFERENCE TO RELATED APPLICATIONS

This application is a 371 National Stage of International Application No. PCT/FR2019/050254, filed Feb. 5, 2019, which claims priority to French Patent Application No. 1851025, filed Feb. 7, 2018, the disclosures of which are herein incorporated by reference in their entirety.

TECHNICAL FIELD

The invention relates to reflection imaging techniques, in particular using probes to be placed close to objects to be analyzed. In this context, the invention explores applications of terahertz waves.

BACKGROUND

The terahertz (THz) wave range is between millimeter waves and visible radiation. It is accepted that the terahertz wave range extends in frequency from about 300 GHz to a few THz. Waves in this range have both radiofrequency and optical properties—in particular, they can be transmitted and received by antennas, and focused by optical systems such as silicon lenses.

THz waves have the property of passing through certain objects without the malignance of X-rays. In medical imaging, they are used, for example, to detect cancerous tissue, since such tissue has different absorption and reflection properties than healthy tissues in the THz range.

The article ["Use of a handheld terahertz pulsed imaging device to differentiate benign and malignant breast tissue", Maarten R. Grootendorst et al, Vol. 8, No. 6, 1 Jun. 2017, Biomedical Optics Express 2932] discloses a handheld probe designed to be moved over a patient's skin and analyze it by wave reflection, similar to an ultrasound probe.

THz waves are implemented in the probe via femtosecond laser pulses generated outside the probe and guided through optical fibers to a photoconductive transmitter/receiver placed inside the probe. Resulting pulses of 0.1 to 1.8 THz are then guided by an oscillating mirror between the transmitter/receiver and a quartz window present at the end of the probe, to scan 26 pixels stepwise, in an area of 15×2 mm at a frequency of 4 Hz. At each step of the scan, reflected THz pulses are returned by the corresponding pixel to the receiver.

Such a handheld probe uses complex and expensive optical technologies. In addition, the pixel pitch of about 0.6 mm provides a relatively low resolution.

This resolution depends on the accuracy of the mirror drive mechanism and the relatively long wavelength of the THz waves. The 0.6 mm pixel pitch corresponds approximately to the Abbe diffraction limit in air for the lowest frequency of the pulses used, here 0.1 THz and a wavelength of 1.2 mm.

Such a system thus requires cumbersome and expensive equipment to implement an image sensor of only 15×2 mm, with the essence of the bulk being taken up by the equipment for producing the required laser beams.

Recently, THz receivers and transmitters have been successfully realized using semiconductor technologies, which are fully exploitable by electronic circuits integrated on the same chips.

THz receivers are thus grouped in an array on a semiconductor chip to form a compact image sensor. For example, the paper ["A 1 k-Pixel Video Camera for 0.7-1.1 Terahertz Imaging Applications in 65-nm CMOS", Richard Al Hadi, Hani Sherry, et al, IEEE Journal of Solid-State Circuits, VOL. 47, NO. 12, December 2012] discloses an image sensor including THz receivers produced entirely in 65-nm CMOS technology. The receivers are able to process signals at frequencies higher than the operating frequency of the transistors through the use of passive elements and configurations where the transistors are less limited in frequency (common source connections). In particular, a power sensing configuration is used—THz waves are received on an antenna and the resulting antenna signal is rectified to charge a capacitor to the peak value of the signal oscillations. Such receivers, known as homodyne receivers, do not provide phase information, but only amplitude information.

It has also been possible to design THz transmitters that are integrable in semiconductor technology, especially CMOS. One difficulty for the transmitters was to produce THz signals having a frequency higher than the operating frequency of the transistors. This difficulty was overcome by using so-called harmonic oscillators. Such an oscillator operates at a frequency compatible with the technology and produces harmonics that can be used in the THz range. U.S. Pat. No. 9,083,324 discloses such an oscillator.

Further information on integrable THz receivers and transmitters can be found in the thesis by Hani Sherry and Richard Al Hadi presented at the University of Wuppertal in 2013.

Despite the demonstrated feasibility of integrating THz components on semiconductor chips, it has not been possible to offer compact reflection sensors that could, for instance, replace the one described in the above-mentioned article of Biomedical Optics Express.

SUMMARY

A sensor for a terahertz imaging system integrally achievable in semiconductor technology is generally disclosed, comprising a flat substrate of semiconductor material transparent to terahertz radiation, configured to be oriented parallel to an object to be analyzed; and a plurality of terahertz radiation receivers arranged in an array on the substrate. The sensor is lensless, and comprises at least one terahertz radiation transmitter arranged on the substrate, so that the radiation emitted by the transmitter is reflected on the object to be analyzed towards the receivers.

The pitch of the array may be at least half the wavelength of the radiation within the substrate, and the transmitter take the place of a receiver in the array.

The receivers may be heterodyne receivers synchronized on a same local oscillator, whereby each receiver provides phase information representative of the distance travelled by the received radiation from the transmitter.

The receivers and transmitter may have a hexagonal configuration and be arranged in a honeycomb matrix.

The sensor may comprise a plurality of transmitters evenly distributed in the array.

The sensor may comprise a tubular support configured to be applied to the object and to maintain the sensor at a fixed distance from the object.

The substrate may have a thickness at most equal to half the wavelength of the terahertz radiation within the substrate, and comprise an active face including metal levels; a back face configured to be oriented towards the object to be analyzed. Each of the receivers and transmitter may then include an annular antenna formed in a metal level of the active face, the average circumference of the antenna being at least half the wavelength of the terahertz radiation within the substrate; and a guard ring surrounding the antenna at the periphery of the receiver or transmitter, formed from metal patterns stacked in several levels of metal.

The guard ring may comprise metal patterns structured to form a cavity housing conductor tracks and electronic components for controlling the receivers and transmitter.

A method of lensless reflection terahertz imaging may use a sensor as disclosed above, and comprise the steps of actuating the transmitter; measuring the signals produced by the receivers in response to the transmitter actuation to form an image in the frequency domain; and performing an inverse Fourier transform on the frequency domain image to produce a space domain image.

Another method of lensless reflection terahertz imaging may use a sensor as disclosed above, and comprise the steps of actuating the transmitters one at a time in a sequence resulting in the illumination of a same area of the object to be analyzed from different angles; measuring the signals produced by the receivers in response to each actuation of the sequence to form a respective image in the frequency domain; and processing the multiple frequency domain images to produce an enhanced space domain image.

The multiple images may be processed by a ptychography technique using only amplitude information provided by the receivers.

The multiple images may be processed by a synthetic aperture microscopy technique using amplitude and phase information provided by the receivers.

BRIEF DESCRIPTION OF THE DRAWINGS

Embodiments will be set out in the following non-limiting description in relation to the attached drawings, among which.

DESCRIPTION OF EMBODIMENTS

Until now, THz transmitter and receiver chips have been considered for use in dissociated devices, in particular arranged on either side of an object to be analyzed by transmission. In this configuration, each device is equipped with an expensive silicon lens, which is also relatively cumbersome compared to the chip dimensions.

If it was proposed in the state of the art to integrate an array of several transmitters on a chip, this was done merely to adapt the emission intensity (and therefore the power consumption) to the measurement conditions by actuating more or less transmitters at the same time (Richard Al Hadi's thesis).

The use of THz receivers on a chip in reflection mode has not been seriously considered in the state of the art, as the most common receivers, power detectors, do not provide phase information, which would cause problems related to specular reflection of the object under analysis, as indicated in the above-mentioned IEEE article.

In spite of this, it is proposed herein to use an array of receivers on a chip in reflection mode, and to integrate transmitters among the receivers on the same chip. Such a configuration seems contrary to preconceived rules at first sight. Indeed, in the neighboring radiofrequency and optical domains, it is not conceivable to place transmitters in the immediate vicinity of the receivers because the transmitters would disturb the neighboring receivers (crosstalk or parasitic reflections).

It turns out that THz waves are relatively easy to contain in a semiconductor chip, and that disturbance problems can be controlled by simple means as described below. As a result, the juxtaposition of a transmitter and a receiver on a chip causes no setbacks if basic precautions are taken. Furthermore, transmitters and receivers can be made to the same dimensions, so that they can be mixed in any way in an array without disturbing the pitch.

Specular reflection in the THz range is in fact a false problem, even when using power detectors (which do not provide phase information for distance evaluation). Indeed, in some applications, just the information of the amount of reflected radiation may be important, since THz waves can differentiate areas by their reflectivity, which corresponds for example to cancer tissue detection applications.

In addition, the resulting imager is considered for use here without a lens, because it appears that lensless imaging techniques used in other areas can then be conveniently applied, as discussed below. This makes the imager particularly well suited for the analysis of a proximate object by reflection, for example at a distance of the order of a centimeter, which eases the design of the transmitters due to the low power required.

Figure 1A:
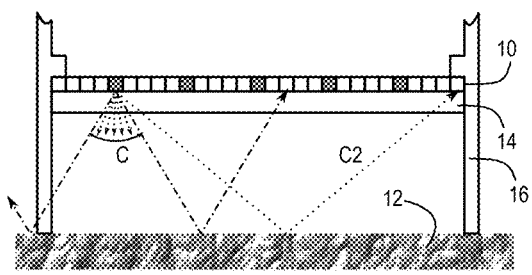
FIGS. 1A to 1C represent, in schematic side views, an embodiment of a THz reflection imager at different stages of the acquisition of a flat area of an object to be analyzed.
Figure 1B:
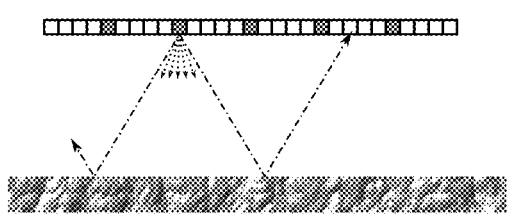
Figure 1C:
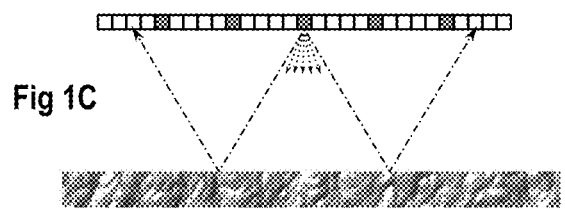

FIGS. 1A to 1C represent, in schematic side views, an embodiment of a THz reflection imager 10 at different stages of the acquisition of a flat area of an object to be analyzed 12.

As shown in particular in FIG. 1A, the imager 10 is formed on a flat substrate of semiconductor material comprising a plurality of pixels arranged in an array. A row of pixels in the array is shown as squares. White squares represent receivers, and gray squares represent transmitters. For example, one out of every five pixels is a transmitter.

The pixel array 10 is formed on a so-called active face of the substrate, which is oriented upwards, opposite to object 12. The thicker part of the substrate 14, called the back-side, faces the object 12. Indeed, THz receivers have better sensitivity, and transmitters produce a stronger signal on the thicker side of the substrate.

The imager may be held at a fixed distance from the object 12 by a tubular support 16, made of a material that preferably does not reflect THz waves. This creates a pen-type probe that can be applied to areas to be analyzed.

In one embodiment, the transmitter pixels are actuated one by one in a sequence—FIGS. 1A to 1C show the actuations of the first three transmitters of the row, starting from the left.

In FIG. 1A, the first transmitter pixel of the row is actuated, the fifth from the left edge. It transmits THz waves within an emission cone C which, depending on the structure of the transmitter, can reach an aperture angle of 90° (an aperture angle of about 60° has been shown as an example). The cone forms a disc on the surface of the object, which is reflected back to the imager in a symmetrical cone. The imager receives a disc twice the diameter of that received by the object, normally centered on the transmitter.

Because the actuated transmitter behaves as a coherent spot source, the disc received by the imager is a spatial Fourier transform, or hologram, of the illuminated area on object 12. This hologram contains amplitude and phase information that allows the reconstruction, by inverse Fourier transform, of a three-dimensional spatial representation of the object as viewed from the actuated transmitter.

Depending on the nature of the materials present in the object, THz waves can be transmitted, absorbed or reflected at varying degrees. Thus, the waves can pass through a transmissive surface of the object and be reflected by materials present at greater depths. The object may be the skin of a patient being investigated for cancerous tissue—cancerous tissue has a higher reflection coefficient than healthy tissue, so it can be differentiated by reflection analysis.

If the phase information of the hologram can be exploited with the help of the receptors, a three-dimensional representation of the reflective tissue can be reconstructed. Alternatively, it is possible to use only the phase information, which in some applications may reveal special properties of the object under analysis.

If only the amplitude information of the hologram can be exploited, for example if the receivers are power detectors, a projection of the reflection levels is still obtained, making it possible to detect more or less reflective areas, and thus detect the outlines of cancerous tissue.

In the shown configuration, with the 60° aperture angle, the disc received in the imager plane does not cover the entire imager, meaning that the imager pixels are underexploited. To improve the hologram accuracy, all the pixels of the imager are preferably used. This can be accomplished by increasing the cone aperture angle, as represented by a line C2, so that the pixel furthest from the imager receives a ray reflected from the edge of the illuminated disk of the object. Alternatively, the imager may be moved away from the object, resulting in the discs being enlarged proportionally to the distance.

With a single transmitter, placed in the center of the imager, it is possible to observe a disk of half the diameter of the imager at most. To cover the entire area of the object in front of the imager, multiple transmitters may be used, distributed throughout the imager, as shown. However, it is not provided to actuate multiple transmitters at the same time, as this would cause complex interference to be processed in the image captured by the imager.

Thus, as shown in FIGS. 1A to 1C for the first three transmitters in the row, it is envisioned to actuate the transmitters one at a time in sequence, and store the resulting images captured by the imager separately.

Figure 2A:
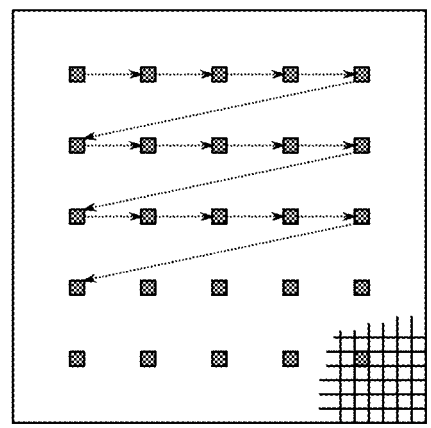
FIG. 2A shows a schematic front view of the imager of FIGS. 1A to 1C, revealing an example of the transmitter structure.

FIG. 2A illustrates, at the scale of FIG. 1A, an extension of this actuation sequence to an exemplary imager viewed from the front, where the transmitters are distributed at a rate of one in five per row and column.

Figure 2B:
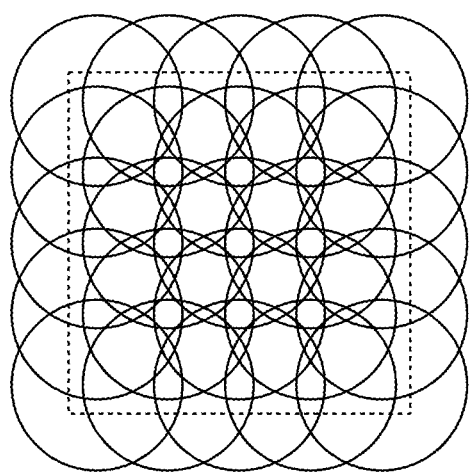
FIG. 2B illustrates a collection of areas illuminated by the imager of FIG. 2A.

FIG. 2B illustrates, at the scale of FIG. 2A, the collection of disks observed on object 12 as a result of the actuation of all the transmitters in FIG. 2A. A square in dotted lines illustrates the actual observed area given the imager's edges.

It turns out that the resulting collection of images captured by the imager, in the Fourier domain, can be processed using techniques known in other fields to reconstruct an image of the entire illuminated area, or even improve the rendering of the object.

The sole amplitude information in the images captured in the example just described may be processed by the so-called ptychography technique, which is used in X-ray imaging to retrieve phase information. Thus, a spatial representation of the object under observation can be reconstructed (here observed by reflection instead of by transmission for X-rays).

The areas of the object that are at the intersection of the largest number of emission cones provide a better three-dimensional rendering, since these areas are illuminated from the largest number of angles. In the example shown in FIG. 2B, these areas are those facing the nine central transmitter pixels of the array.

Thus, to improve three-dimensional rendering, the transmission angles can be enlarged or the imager can be moved away from the object. This extends the areas of intersection of the emission cones and leads to an optimal configuration where a central area of interest of the object is located at the intersection of all the cones. Of course, the reception angle of the receivers may be considered—in the THz range, receivers and transmitters have similar structures leading to similar transmission and reception angles of up to 90°.

The number of transmitter pixels may be increased to improve three-dimensional rendering. However, each transmitter pixel replaces a receiver pixel in the array, so that the image captured by the imager has a "black" pixel at that location. The values of such black pixels may be interpolated from adjacent receiver pixels. A trade-off can be achieved between the improvement gained by increasing the number of transmitters and the loss of detail produced by the imager due to the decrease in the number of receiver pixels.

In the configuration shown in FIG. 1A, the imager is at a known distance from the object. This allows the angle of incidence of the radiation reaching each receiver to be calculated as a function of the coordinates of the receiver and the actuated transmitter. Based on the known sensitivity and power lobes of the receiver and transmitter, the measured intensity can be corrected and the effective angle of the transmitter and receiver cones can be increased.

If the receivers allow phase measurement, a technique called Synthetic Aperture Microscopy (SAM) can be used. Such a technique is described, for example, in the article ["Theory of the Synthetic Aperture Microscope", Terry Turpin et al, SPIE Proceedings, Vol. 2566B-34, July 1995, San Diego]. This technique aims at reconstructing an accurate three-dimensional representation of the observed object from views from different angles and the depth (phase) information obtained in each view. Since the phase information is not limited by wavelength or pixel pitch, it is possible to reconstruct a three-dimensional representation with a resolution that tends towards the accuracy of the phase measurement. From the three-dimensional representation, slices can be extracted whose resolution exceeds the Abbe diffraction limit or the pixel pitch.

Note that in the THz range, phase can be measured directly with the aid of electronic circuitry, whereas in the optical domain of microscopes, phase is measured by the interference of two coherent beams. Thus, in the above-mentioned SPIE Proceedings article, a complex optical system is disclosed to make a main laser beam interfere with a laser beam reflected from the object to be analyzed, emitted by a coherent source which, thanks to a mechanical system, illuminates the object at a multitude of angles in sequence.

Thus, the use of the SAM technique involves the use of THz receivers capable of measuring phase, for example heterodyne receivers. The paper ["A Fully Integrated 320 GHz Coherent Imaging Transceiver in 130 nm SiGe BiCMOS", Chen Jiang et al, IEEE Journal of Solid-State Circuits, Vol. 51, No. 11, November 2016] and Hani Sherry's thesis describe implementations of heterodyne THz receivers in semiconductor technology. A heterodyne receiver mixes the signal from a fixed local oscillator and the received THz signal to produce an intermediate frequency (frequency difference) signal that can be exploited on the chip and carries the phase information. The local oscillator signal can be produced in the same way as the signal of the transmitters (e.g. a harmonic oscillator), by selecting a frequency slightly offset so that the intermediate frequency is not zero. This can be achieved by using two oscillators of same structure, but supplied with different voltages to achieve the offset. It is also possible to use two phase-locked loops using the same reference frequency, but with different multiplication factors.

The intermediate frequency signal then has an amplitude proportional to the amplitude of the received THz signal and a phase equal to the phase to be measured. All the imager's receivers are then supplied by the same local oscillator so that they are synchronous and have the same reference for measuring the phase.

Figure 3:
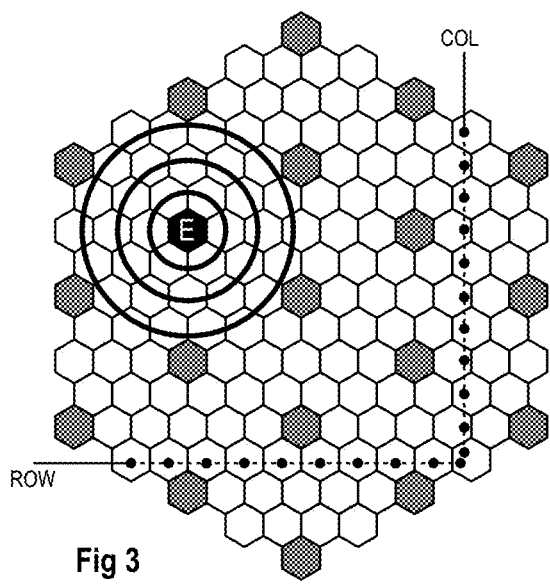
FIG. 3 shows a schematic front view of another embodiment of a THz reflection imager including hexagonal transmitter and receiver pixels arranged in a honeycomb matrix.

FIG. 3 shows a schematic front view of another embodiment of a THz reflection imager. The imager includes hexagonal transmitter and receiver pixels arranged in a honeycomb matrix. The matrix includes lines of contiguous pixels along three main axes: at 0° (horizontal), 120°, and 240°. Along each main axis, one pixel out of six is a transmitter pixel. The transmitter pixels are further distributed in the matrix so that each one is equidistant from the other six nearest transmitter pixels, which are arranged at the vertices of a hexagon.

The hexagonal configuration of the pixels is particularly well adapted to the structure of the THz transmitters and receivers under consideration. Indeed, the transmitters and receivers may be based on a ring antenna, as discussed below, and the hexagonal structure is more compact than a square structure to accommodate a ring antenna. In addition, because the matrix is honeycombed, it can accommodate a larger number of pixels for a given pitch between pixels. These features combined result in significantly higher resolution for a given pitch than a square array and better rendering of oblique lines.

In addition, the honeycomb structure proves to offer better accuracy in the intended application. As shown for a transmitter E, the transmitter emits in a cone which is reflected towards the transmitter and the receivers surrounding it in concentric rings, assuming that the surface of the object is substantially flat. The rings can be considered as rings of equal intensity, the value of the intensity decreasing radially from the center, according to the transmitter's power emission lobe. Each ring can be contained, as shown, in contiguous pixels forming a hexagonal contour that closely approximates the ring. This allows, among other things, a better rendering of concentric patterns characteristic of a spatial Fourier transform and a more uniform application of an intensity correction factor as a function of the angle of incidence.

Controlling the pixels of the honeycomb matrix does not pose particular problems compared to pixels of a square matrix. As shown as an example, the pixels in each 0° line can be controlled by row lines ROW, and the pixels belonging to each pair of adjacent 90° diagonals can be controlled by column lines COL. The particular management of THz receivers and transmitters in an array is known and will not be described in more detail here.

Figure 4:
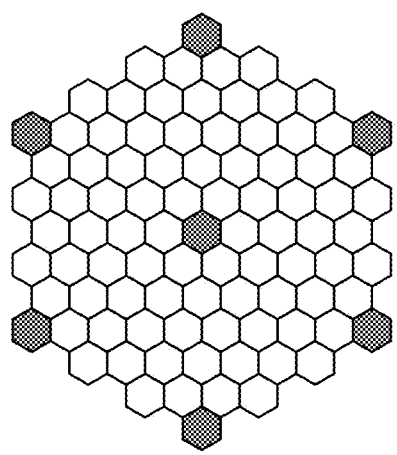
FIG. 4 shows a schematic front view of an alternative honeycomb imager.

FIG. 4 illustrates another example of distribution of transmitters in a honeycomb matrix. Whereas in FIG. 3 each transmitter was surrounded by three complete concentric hexagons, here each transmitter is surrounded by five complete concentric hexagons.

Figure 5:
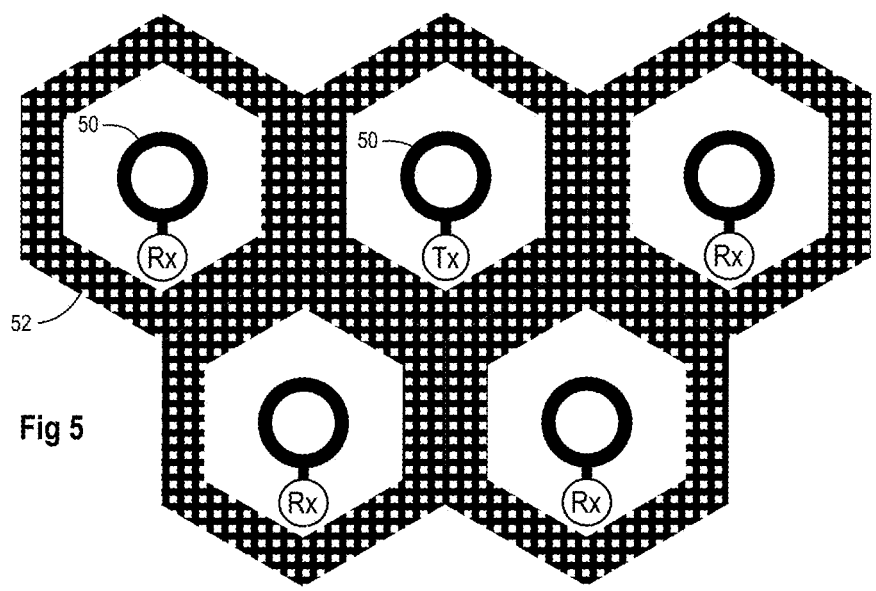
FIG. 5 represents an enlarged top view of an embodiment of hexagonal pixels produced in a semiconductor technology.

FIG. 5 shows an enlarged partial top view of an embodiment of hexagonal pixels fabricated in a semiconductor technology, e.g. 65 nm CMOS. A transmitter pixel Tx is shown surrounded by four adjacent receiver pixels Rx. The elements in this view are depicted substantially to scale for an imager designed to work at about 600 GHz, as an example. As can be seen, all pixels, both receiver and transmitter, are identical in size.

The frequency of 600 GHz corresponds to a wavelength of 0.5 mm in air. The pixels are integrated in a silicon substrate, where the wavelength decreases by a multiplication factor of about 0.6, reducing the wavelength to about 0.3 mm in silicon. Furthermore, it is acceptable to work at only half the wavelength, i.e. 0.15 mm, as this allows the resolution to be increased by a factor of 2 with an acceptable loss of gain. Thus, the antennas of the transmitters and receivers are sized to work at this wavelength. The antennas 50 here are annular, which implies that their average circumference is at least equal to the working wavelength, i.e. 0.15 mm.

The rings are etched, for example, in the last metal layer of the technology and have a width of 10 µm, i.e. an external diameter of 64 µm and an internal diameter of 54 µm.

In addition, to prevent the transverse propagation of electrical disturbances by inductive or capacitive coupling between pixels, each pixel includes a peripheral guard ring 52, which can be circular or, here, hexagonal. The antenna is centered in a predominantly metal-free area with an average diameter approximately equal to the working wavelength (0.15 mm). Thus, the inner edge of the guard ring is at least 38 µm away from the outer edge of the antenna ring. The guard ring is also 30 µm wide, and is structured to meet a metal/void ratio recommended by the technology. The pixel thus has a width of 200 µm between two opposite sides of the hexagon, a value corresponding to the pitch along each of the three axes at 0°, 120° and 240°.

Figure 6:
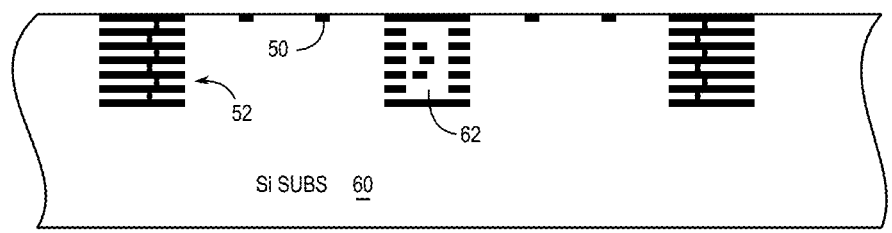
FIG. 6 is a cross-section view of an example of the pixel configuration of FIG. 5.

FIG. 6 is a cross-section view of the pixels of FIG. 5. The pixels are formed on the active face of a semiconductor substrate 60, here made of silicon. The antennas 50, etched in the last metal level, are flush with the upper side of the substrate. This upper side is normally covered with a passivation layer, not shown. The guard rings 52, as shown, may be extended in depth using metal patterns stacked in all the metal levels of the technology, seven in 65 nm CMOS, interconnected by vias. The vias may be arranged around each pixel at a pitch that perfects the screening function.

The thickness of the substrate 60 may be chosen to limit internal reflections of THz waves on the back-side of the substrate, especially waves produced by transmitters that could disturb neighboring receivers. This is achieved with a thickness at most equal to half the wavelength in silicon, i.e. 0.15 mm.

The guard rings and the choice of a specific substrate thickness overcome, in the THz range, any interference problems that could arise from the integration of a transmitter within an array of receivers.

As shown for a wall of one of the guard rings, the metal patterns can be structured to form a cavity 62. Cavity 62 may accommodate conductor tracks and electronic components for controlling the pixels. In fact, the width of two adjacent guard rings is of the order of 60 µm, which, in 65 nm technology, provides sufficient space to accommodate the majority of the conductors and electronic components required to locally exploit the pixels. This configuration reduces to a strict minimum the metallic conductors in the empty areas around the antennas, which would disturb the optical properties.

The invention claimed is:

1. A sensor for a terahertz imaging system integrally achievable in semiconductor technology, comprising:
   an analysis area;
   a flat substrate of semiconductor material located at a distance from the analysis area, with no lens interposed between the substrate and the analysis area;
   a plurality of terahertz radiation receivers arranged in an array on the substrate; and
   a plurality of terahertz radiation transmitters distributed in the array such that each transmitter is separated by multiple receivers, the distance between the substrate and the analysis area being such that radiation emitted by the transmitter is reflected by the analysis area towards multiple receivers, whereby the multiple receivers are presented together with an image in the frequency domain.

2. The sensor according to claim 1, wherein a pitch of the array is at least half a wavelength of the radiation within the substrate, and each transmitter takes the place of a receiver in the array.

3. The sensor according to claim 2, wherein the receivers and transmitters have a hexagonal configuration and are arranged in a honeycomb matrix.

4. The sensor according to claim 2, comprising a tubular support configured to be applied to an object to analyze and to maintain the substrate at a fixed distance from the object.

5. The sensor according to claim 2, wherein the substrate has a thickness at most equal to half the wavelength of the terahertz radiation within the substrate, and comprises:
   an active face including metal levels;
   a back face oriented towards the analysis area; and
   each of the receivers and transmitters includes:
      an annular antenna formed in a metal level of the active face, an average circumference of the antenna being at least half the wavelength of the terahertz radiation within the substrate; and
      a guard ring surrounding the antenna at the periphery of the receiver or transmitter, formed from metal patterns stacked in several levels of metal.

6. The sensor according to claim 5, wherein the guard ring comprises metal patterns structured to form a cavity housing conductor tracks and electronic components for controlling the receivers and transmitter.

7. The sensor according to claim 1, wherein the receivers are heterodyne receivers synchronized on a same local oscillator, whereby each receiver provides phase information representative of a distance travelled by the received radiation from the transmitter.

8. A method of reflecting terahertz imaging using a lensless sensor, the sensor comprising a substrate of semiconductor material, a plurality of terahertz radiation receivers arranged in an array on the substrate, and a plurality of terahertz radiation transmitters evenly distributed in the array such that each transmitter is separated by multiple receivers, the method comprising:
   locating the substrate at a distance from an object to be analyzed without interposing a lens between the substrate and the object;
   actuating the transmitters one at a time in a sequence resulting in the illumination of a same area of the object to be analyzed from different angles;
   directly acquiring a respective image from signals produced by the receivers in response to each actuation of the sequence; and
   processing the respective images to produce an enhanced space domain image.

9. The method according to claim 8, wherein the respective images are processed by a ptychography technique using only amplitude information provided by the receivers.

10. The method according to claim 8, wherein the respective images are processed by a synthetic aperture microscopy technique using amplitude and phase information provided by the receivers.

* * * * *